(12) United States Patent
Ferragamo et al.

(10) Patent No.: US 8,672,970 B2
(45) Date of Patent: Mar. 18, 2014

(54) ANCHORING SYSTEM

(71) Applicant: Smith & Nephew, Inc., Andover, MA (US)

(72) Inventors: Michael C. Ferragamo, Foster, RI (US); Bernard J. Bourque, Taunton, MA (US); William R. Davis, Hingham, MA (US)

(73) Assignee: Smith & Nephew, Inc., Andover, MA (US)

( * ) Notice: Subject to any disclaimer, the term of this patent is extended or adjusted under 35 U.S.C. 154(b) by 0 days.

(21) Appl. No.: 13/873,945

(22) Filed: Apr. 30, 2013

(65) Prior Publication Data
US 2013/0238026 A1 Sep. 12, 2013

Related U.S. Application Data

(62) Division of application No. 12/333,025, filed on Dec. 11, 2008, now Pat. No. 8,454,654.

(60) Provisional application No. 61/013,342, filed on Dec. 13, 2007.

(51) Int. Cl.
*A61B 17/04* (2006.01)
*F16B 35/02* (2006.01)
*F16B 13/12* (2006.01)

(52) U.S. Cl.
USPC .......................................................... 606/232

(58) Field of Classification Search
USPC ......... 606/232, 280–299, 300, 301, 304, 313, 606/319, 326–328; 623/13.11–13.2, 623/17.11–17.16; 411/16–18, 44–74, 411/80.1–80.2
See application file for complete search history.

(56) References Cited

U.S. PATENT DOCUMENTS

| | | | | |
|---|---|---|---|---|
| 5,125,840 | A | * | 6/1992 | Durr et al. ...................... 433/173 |
| 5,702,397 | A | * | 12/1997 | Goble et al. ................... 606/232 |
| 5,957,953 | A | * | 9/1999 | DiPoto et al. ................. 606/232 |
| 7,955,388 | B2 | * | 6/2011 | Jensen et al. ............... 623/13.14 |
| 8,202,295 | B2 | * | 6/2012 | Kaplan .......................... 606/232 |
| 8,454,654 | B2 | * | 6/2013 | Ferragamo et al. ........... 606/232 |
| 2004/0136802 | A1 | * | 7/2004 | Lin et al. ....................... 411/57.1 |
| 2005/0075668 | A1 | * | 4/2005 | Lizardi .......................... 606/232 |
| 2006/0246396 | A1 | * | 11/2006 | Suttin et al. ................... 433/173 |
| 2006/0253119 | A1 | * | 11/2006 | Berberich et al. ............... 606/72 |
| 2006/0282083 | A1 | * | 12/2006 | Fanton et al. ................... 606/72 |

* cited by examiner

*Primary Examiner* — Matthew Lawson
(74) *Attorney, Agent, or Firm* — Pierce Atwood LLP; Joseph M. Maraia

(57) ABSTRACT

The present disclosure relates to an anchor assembly. The anchor assembly includes an anchor defining a cavity and an opening to the cavity and an insertion member including a body having a proximal end portion and a flat distal end portion, and a head coupled to the proximal end portion of the body. The insertion member is configured for arrangement within the anchor cavity. A method of tissue repair and other anchor assemblies are also disclosed.

7 Claims, 11 Drawing Sheets

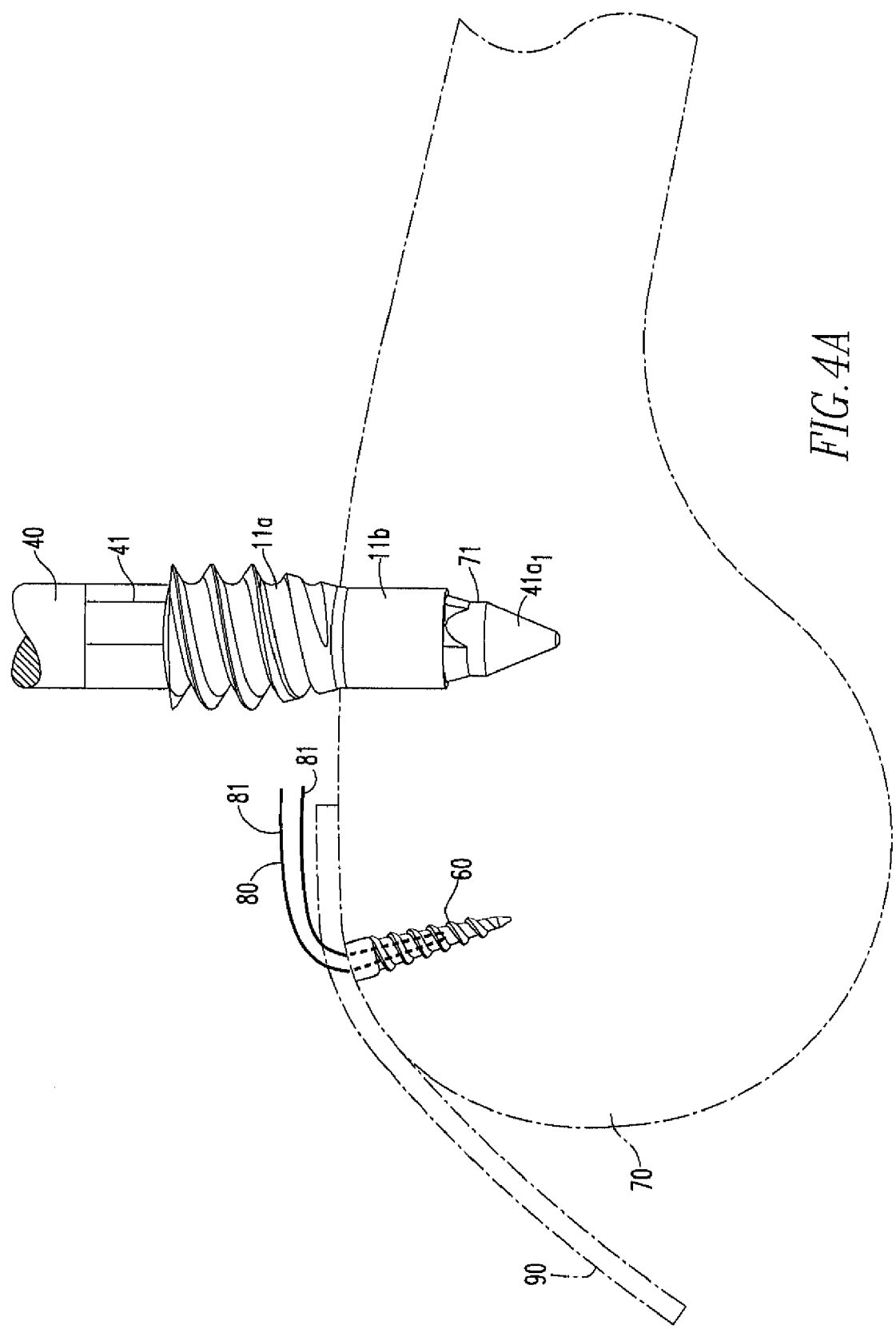

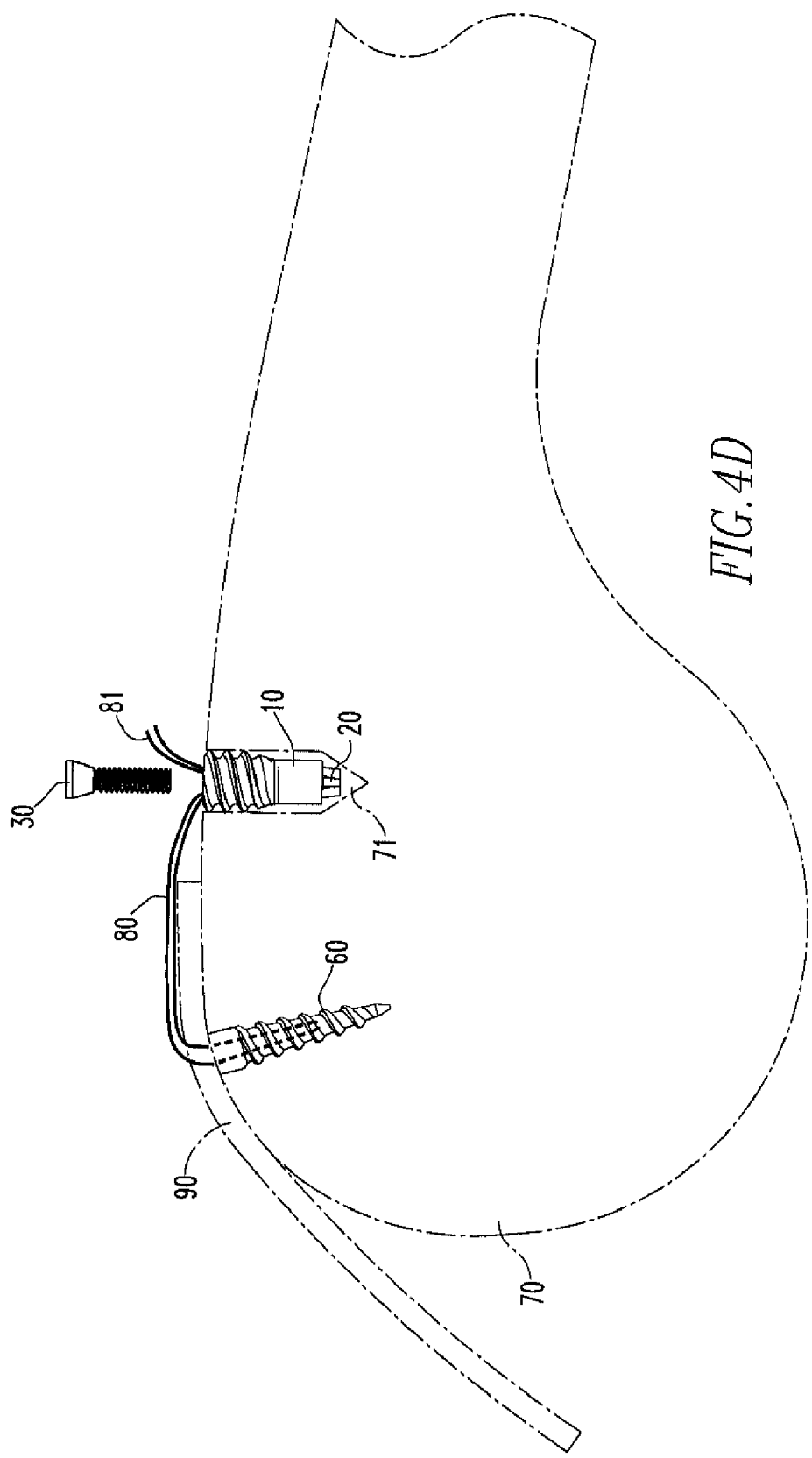

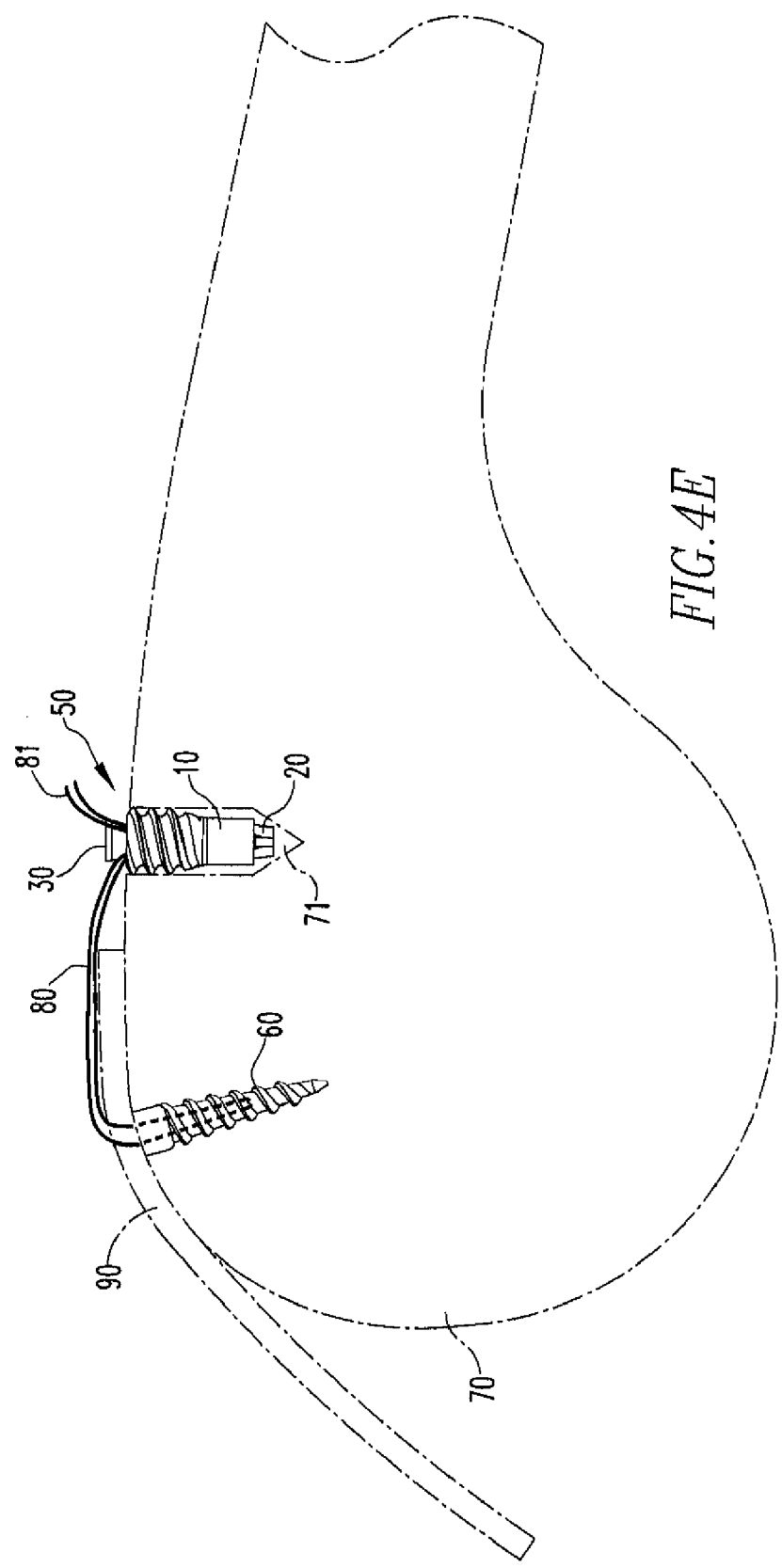

ANCHORING SYSTEM

CROSS-REFERENCE TO RELATED APPLICATIONS

Related Application

This application is a Divisional of U.S. application Ser. No. 12/333,025, filed Dec. 11, 2008, which claims the benefit of U.S. Provisional Application No. 61/013,342, filed Dec. 13, 2007, the disclosure of which are incorporated herein by reference in its entirety.

BACKGROUND

1. Field of Technology

The present disclosure relates to tissue repair, and more specifically, to an anchoring system for securing tissue to bone.

2. Related Art

Arthroscopic procedures often require soft tissue to be reattached to bone. To achieve this, anchors are placed in the bone and sutures attached to the anchor are passed through the tissue to securely retain the tissue in place. When making a repair of soft tissue to bone, it is advantageous to have as large an area of contact between the bone and tissue as possible. Anchor points spaced from one another in rows result in a repair having a broader area of contact. A procedure, and components for use in such procedure, that securely attaches tissue to bone using a plurality of attachment points over a large area of contact is needed. Such procedure must be able to be done in a quick and efficient manner with a minimum of recovery time for the patient.

SUMMARY

In one aspect, the present disclosure relates to an anchoring system including an anchor having an internal bore, a plug disposed within the internal bore of the anchor and wherein the plug has an internal cavity, and a locking member disposed within the internal cavity of the plug. In an embodiment, the plug further includes a transverse hole. In another embodiment, the anchoring system further includes a flexible member disposed within the hole of the plug. In a yet another embodiment, the flexible member includes a suture. In a further embodiment, the transverse hole includes a through hole. In yet a further embodiment, the flexible member is disposed within the through hole of the plug.

In an further embodiment, the internal bore of the anchor is configured for receiving a delivery device. In another embodiment, the anchor includes a groove located on an inner wall of the anchor. In yet another embodiment, the plug is wedge-shaped. In a further embodiment, the plug includes at least one tab. In yet a further embodiment, the tab is expandable. In an embodiment, the plug includes at least two tabs, the tabs located on opposite sides of the plug. In another embodiment, the two tabs are expandable. In yet another embodiment, the internal cavity of the plug includes surface features. In a further embodiment, the surface features include threads. In yet further embodiment, the anchor includes surface features located on an outer surface of the anchor. In an embodiment, the surface features include threads. In another embodiment, the locking member includes a head and a shaft coupled to the head, wherein the shaft includes surface features configured for engagement with the surface features of the internal cavity of the plug. In yet another embodiment, the surface features of the shaft include threads.

In another aspect, the present disclosure relates to a method of tissue repair. The method includes inserting a first anchor into bone, wherein the first anchor includes a flexible member coupled thereto; passing ends of the flexible member through the tissue; inserting a second anchor into the bone, the second anchor including an internal bore; providing a plug including an internal cavity and a transverse hole; passing at least one end of the flexible member into the hole of the plug; and inserting the plug into the internal bore of the second anchor.

In an embodiment, the method further includes inserting a locking member into the internal cavity of the plug to secure the flexible member within the internal bore of the second anchor and the tissue to the bone. In another embodiment, the method further includes tensioning the flexible member before placing the locking member within the plug cavity. In yet another embodiment, the plug includes at least one tab. The tab expands into a groove located on an inner wall of the second anchor upon insertion of the locking member into the internal cavity of the plug. In a further embodiment, the transverse hole includes a through hole. In yet a further embodiment, the method further includes passing the one end of the flexible member into the through hole. In an embodiment, the plug includes at least two tabs, the tabs located on opposite sides of the plug and wherein the tabs expand into the groove upon insertion of the locking member into the internal cavity of the plug. In another embodiment, the method further includes removing the locking member from the plug and tensioning the flexible member.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIGS. 4A-4E show use of the anchoring system of the present disclosure in repairing tissue.

DETAILED DESCRIPTION OF THE EMBODIMENTS

Figure 1A:
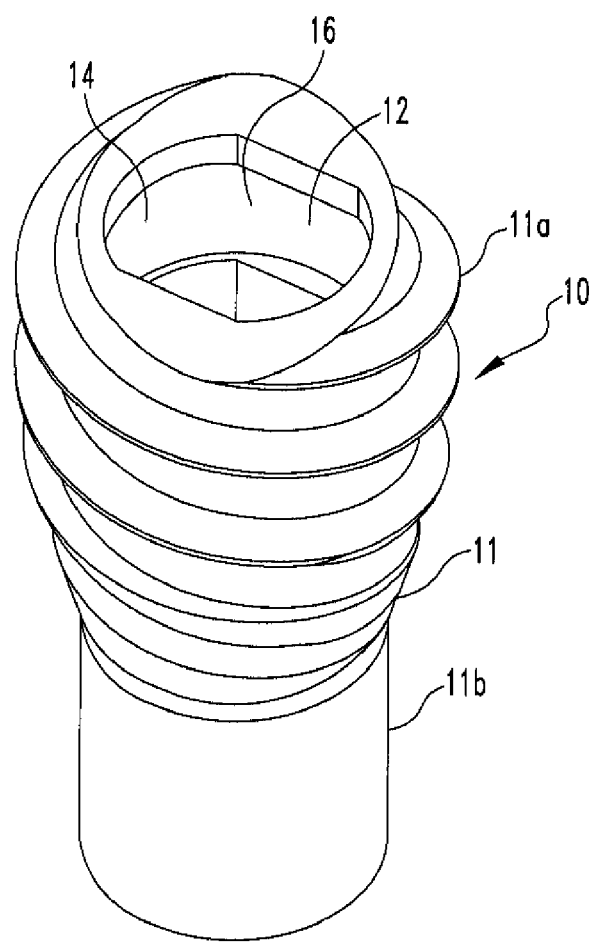
FIG. 1A shows a perspective view of the anchor of the present disclosure.
Figure 1B:
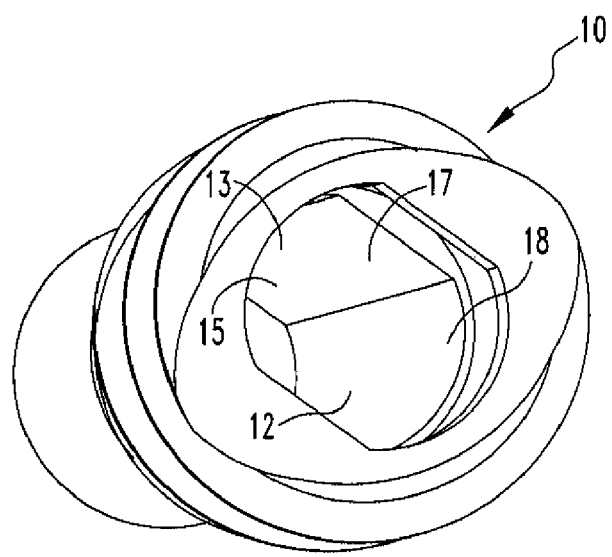
FIG. 1B shows a top view of the anchor of the present disclosure.

The following description of the preferred embodiment(s) is merely exemplary in nature and is in no way intended to limit the disclosure, its application, or uses, FIGS. 1A and 1B show the anchor 10 of the present disclosure. The anchor 10 includes an outer wall 11 having a proximal portion 11a including surface features, such as threads, and a distal portion 11b. The anchor 10 also includes an internal bore 12 extending a length of the anchor 10. A wall 13 of the bore 12 includes a proximal portion 14 and a distal portion 15. The proximal portion 14 includes a groove 16. The distal portion 15 includes a first surface 17 and a second surface 18. The first surface 17 is flat and the second surface 18 is arc-shaped. The distal portion 15 is configured for receiving a delivery device and a plug, as further discussed below.

Figure 2A:
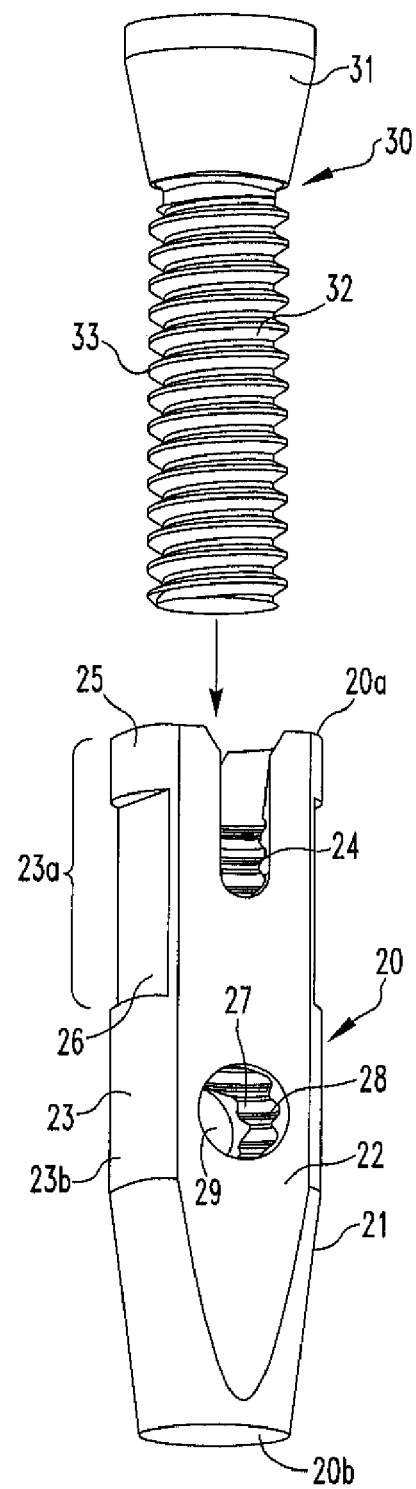
FIG. 2A shows an exploded view of the plug and locking member of the present disclosure.
Figure 2B:
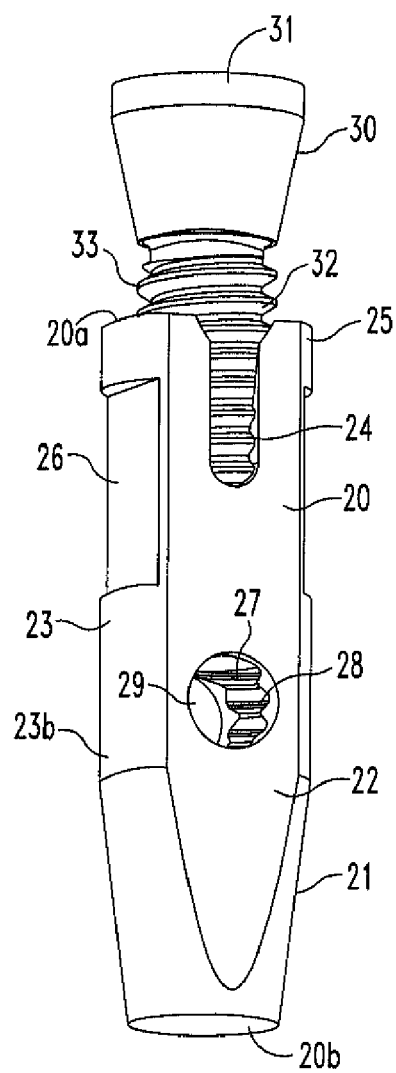
FIG. 2B shows a side view of the plug and locking member of the present disclosure.

FIGS. 2A and 2B show the plug 20 and the locking member 30 of the present disclosure. The plug 20 is substantially wedge-shaped and includes a proximal end 20a and a flat distal end 20b. An outer wall 21 of the plug 20 includes a first surface 22 and a second surface 23. The first surface 22 is substantially flat and includes a slot 24. The second surface 23 includes a proximal end 23a and a distal end 23b. The distal end 23b is substantially arc-shaped and the proximal end 23a includes tabs 25 and a recessed portion 26 located between the tabs 25 and the distal end 23b. The recessed portion 26 allows the tabs 25 to expand, as will be further described below. Although FIGS. 2A and 2B show two tabs 25, a higher or lesser number of tabs 25 may be present. The first and second surfaces 22,23 are configured to allow the surfaces 22,23 to conform to the surfaces 17,18 of the plug distal portion 15, thereby allowing for easier receipt of the plug 20 into the internal bore 12 of the anchor 10, as will be further described below. The plug 20 also includes an internal cavity 27 having surface features 28, such as threads, and a transverse through hole 29. The cavity 27 extends into the through hole 29.

The locking member 30 includes a head 31 and a shaft 32 coupled to the head 31. The shaft 32 includes surface features 33, such as threads, configured for engagement with the threads 28 of the plug 20 when the locking member 30 is disposed within the plug 20, as shown in FIG. 2B.

Figure 3A:
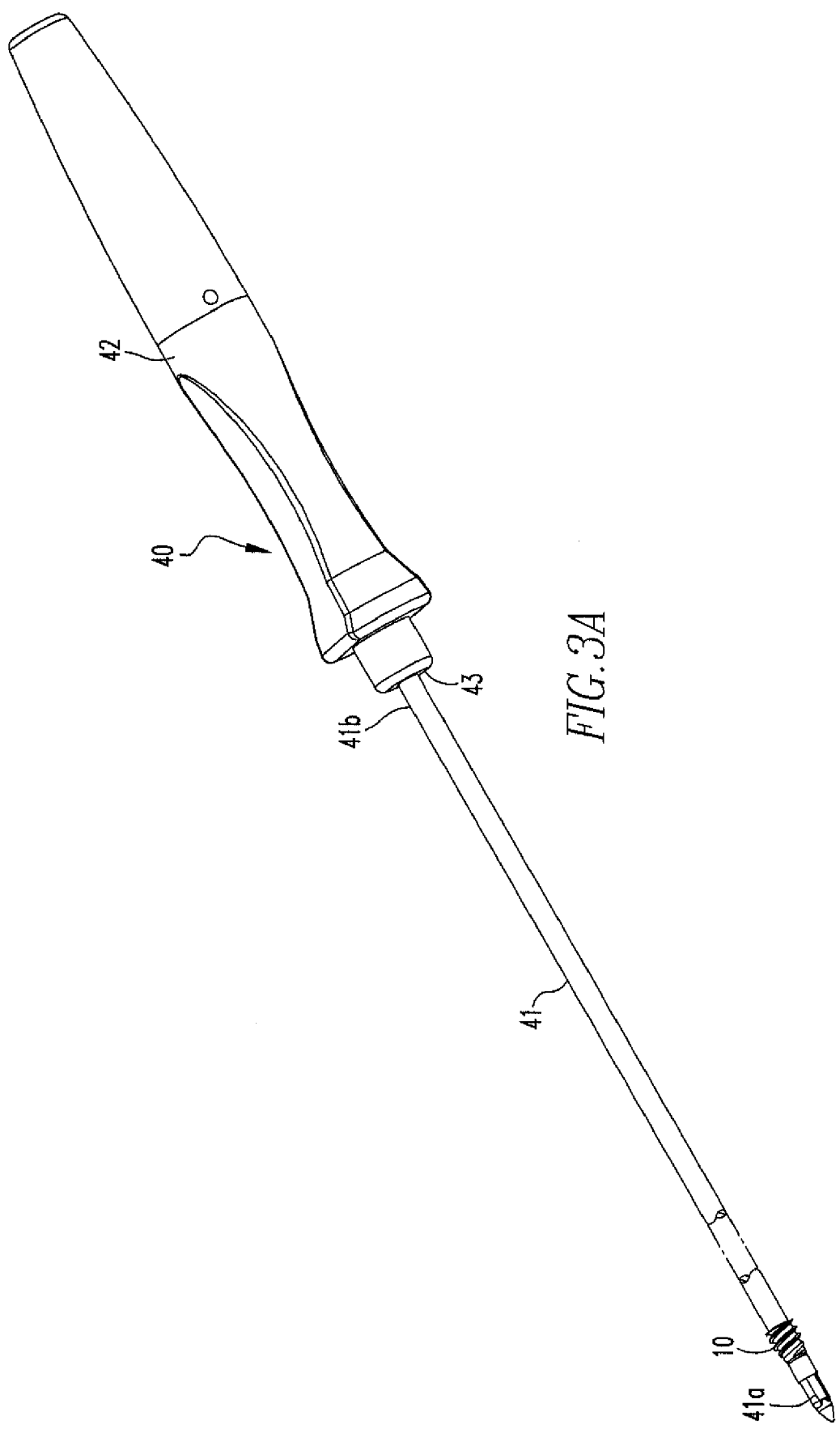
FIG. 3A shows perspective view of a delivery device having the anchor of the present disclosure disposed on a shaft of the delivery device.
Figure 3B:
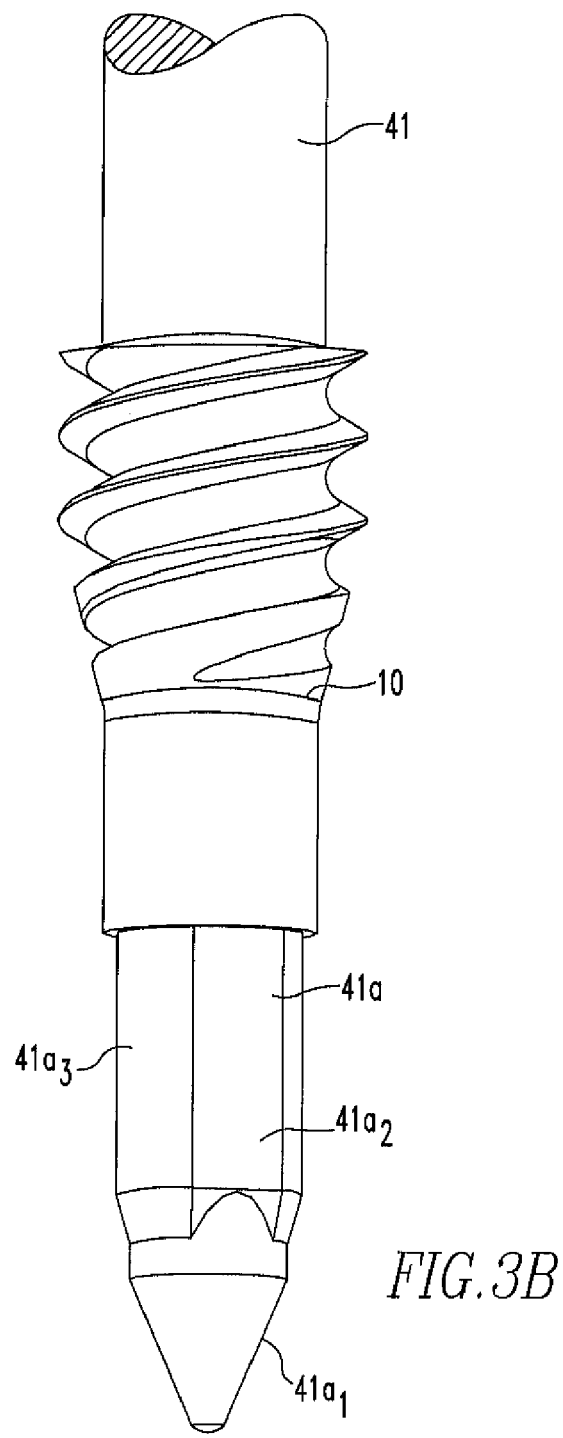
FIG. 3B shows a side view of the anchor of the present disclosure disposed on the shaft of the delivery device.

The anchor 10 of the present disclosure may be used in conjunction with another anchor to repair soft tissue. FIGS. 3A and 3B show the anchor 10 located on the shaft 41 of a delivery device 40 in preparation for insertion of the anchor 10 into bone, as will be more fully described below. The delivery device 40 will includes the shaft 41 having a distal portion 41a, configured for engagement with the internal bore 12 of the anchor 10, and a proximal portion 41b coupled to a handle 42. As shown in FIG. 3B, the distal portion 41a includes a pointed end $41a_1$, a first surface $41a_2$, and a second surface $41a_3$. The first and second surfaces $41a_2, 41a_3$ are configured to allow the surfaces $41a_2, 41a_3$ to conform to the surfaces 17,18 of the internal bore 12, thereby allowing for easier receipt of the internal bore 12 onto the distal portion 41a.

Figure 4B:
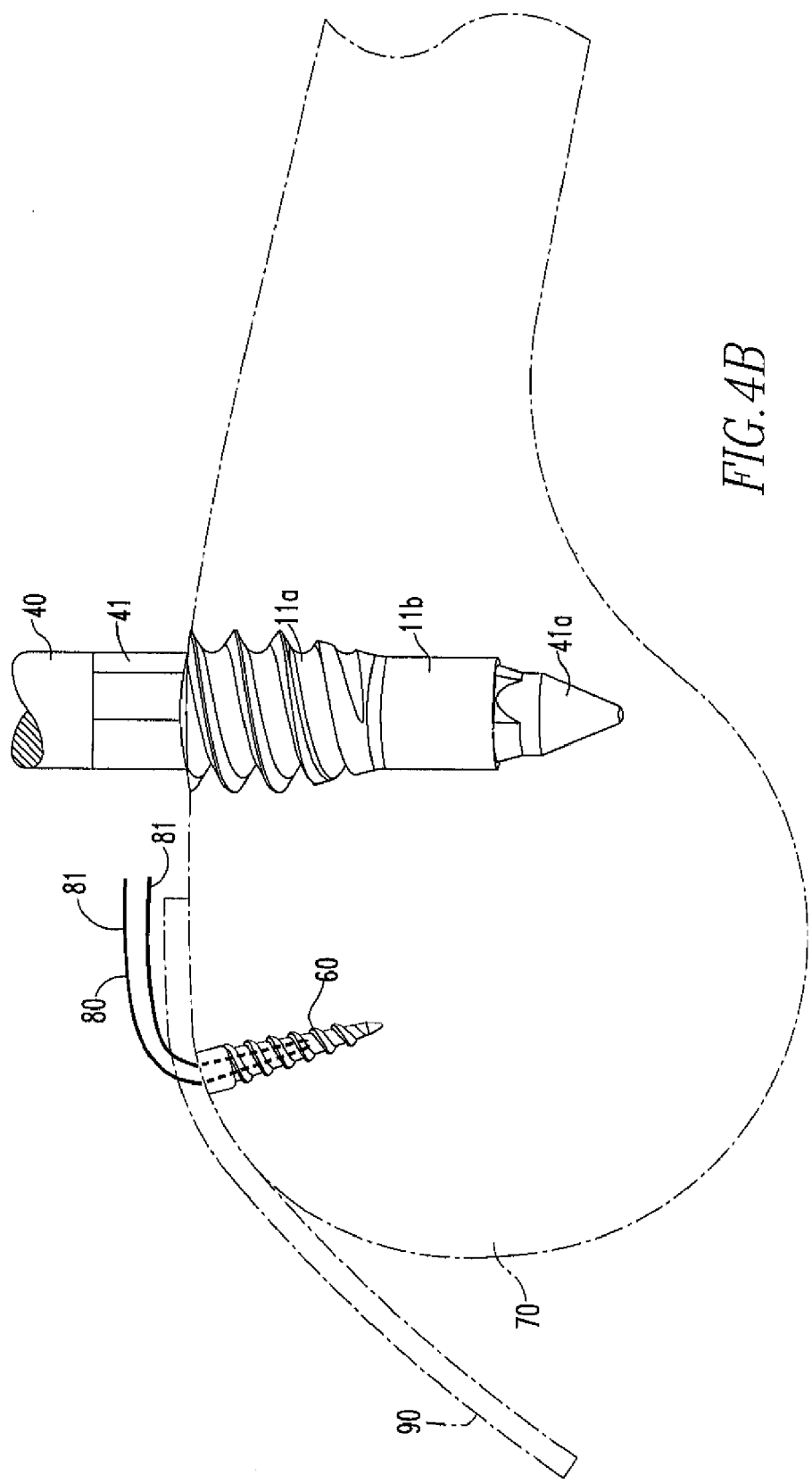

FIGS. 4A-4E show the anchoring system 50 in use during arthroscopic repair of the rotator cuff. However, the anchoring system 50 may be used in the repair of soft tissue in other parts of the body. FIG. 4A shows a first anchor 60 that has been inserted into the lateral aspect of a bone 70, such as a humeral bone. The anchor 60, which has a flexible member 80, such as a suture, coupled thereto, is inserted into the bone 70, a soft tissue 90, such as a rotator cuff tendon, is placed on the bone 70 to be located adjacent to the anchor 60, and the ends 81 of the flexible member 80 are placed through the soft tissue 90.

Next, the delivery device 40 is used to place a second anchor, such as the anchor 10 of the present disclosure, into the medial aspect of the bone 70. The pointed end of $41a_1$ of the shaft 41 is used as an awl to start the hole 71, by tapping the handle 42 with a surgical mallet, or other axially oriented, advancement force. The delivery device 40 is axially advanced into the hole 71 until the distal portion 11b of the anchor 10 is no longer exposed, as shown in FIG. 4A. The delivery device 40 is then rotated until the proximal portion 11a of the anchor 10 is no longer exposed, as shown in FIG. 4B. The delivery device 40 allows for the creation of the hole 71 and insertion of the anchor 10 in one step, rather than multiple steps. The delivery device 40 and anchor 10 are shown in an enlarged view compared to FIGS. 4C-4E where the anchor 10 is much smaller in size. The anchor 10 and delivery device 40 are shown in an enlarged view merely for the purposes of an increased level of detail and for further understanding of the repair process.

Figure 4C:
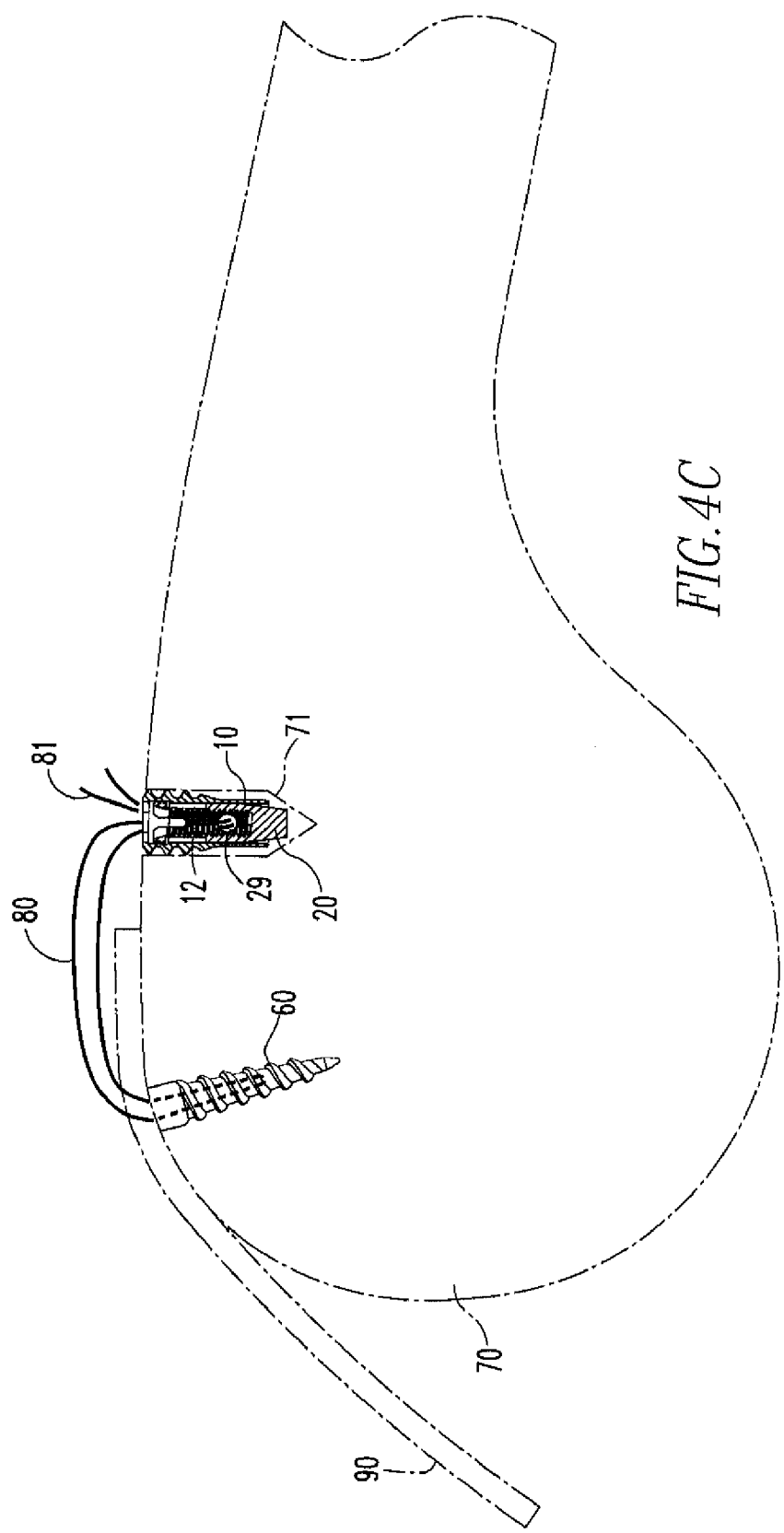

Subsequent to the anchor 10 being placed in the bone 70, the delivery device 40 is removed, and at least one end 81 of the flexible member 80 is passed through the transverse through hole 29 of the plug 20. The plug 20 is then placed into the internal bore 12 of the anchor 10, as shown in FIG. 4C, such that the ends 81 extend out of the hole 71. After placement of the plug 20 into the anchor 10, the ends 81 of the flexible member 80 may be pulled to provide a preferred amount of tension on the flexible member 80 and the soft tissue 90. This tension on the flexible member 60 can be seen in FIG. 4D, especially when comparing these figures to FIG. 4C. As shown in FIGS. 4D and 4E, after insertion of the plug 20 into the inner bore 12 of the anchor 10, the locking member 30 is advanced into the internal cavity 27 of the plug 20, such that, as will be further described below, the plug 20 expands to lock the plug 20 within the inner bore 12 of the anchor 10. In addition, advancement of the locking member 30 secures the flexible member 80 within the through hole 29 and the internal bore 12 and secures the tissue 90 to the bone 70.

Figure 5:
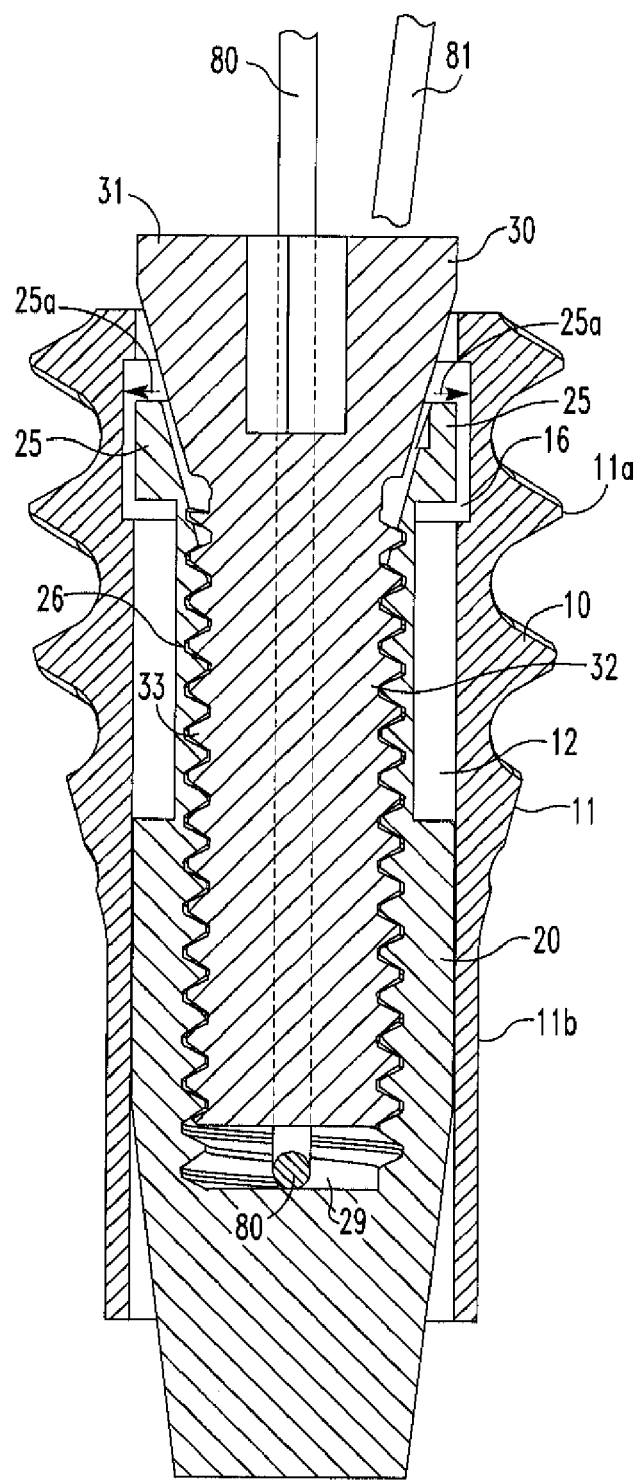
FIG. 5 shows a cross-sectional view of the anchoring system of the present disclosure.

As shown in FIG. 5, advancement of the locking member 30 into the inner bore 12 causes the tabs 25 to expand outward 25a and into the groove 16 of the bore 12, thereby locking the plug 20 within the bore 12. Also shown is the impingement of the locking member 30 on the flexible member 80, which secures the flexible member 80 within the through hole 29. Both the plug 20 and the locking member 30 are advanced via delivery tools that provide for axial and rotary advancement. The suture 80 may need to be retensioned subsequent to placing the locking member 30 into the plug 20. If re-tensioning is necessary, the delivery tools may be used to remove the locking member 30, so that tension mat be applied to the suture 80. The locking member 30 would then be re-inserted into the plug 20.

The anchor 10 and plug 20 of the present disclosure and the first anchor 60 are made from a bioabsorbable polymer material via an injection molding process. However, other materials and processes may be used. In addition, the suture material is made from a bioabsorbable polymer material, but other material may be used. Also, the initial anchor, such as the first anchor 40 shown above, may include more than one suture and the sutures may be secured together at one attachment point, such as within the second anchor 10 shown above, or independently at more than one attachment point. For the purposes of this disclosure, the locking member 30 is made from a biocompatible material, such as titanium, stainless steel, or polyetheretherketone (PEEK). However, the locking member 30 may be made from other absorbable or non-absorbable material.

Furthermore, the proximal portion 11a of the anchor 10 may include features other than threads to reduce the possibility of removal of the anchor 10 and the threads may extend the entire length of the anchor 10. Similarly, the outer wall 21 of the plug 20 and the internal bore 12 of the anchor 10 may include surface features other than those shown and described to facilitate insertion and removal of the anchor 10 onto the shaft 41 and the plug 20 within the internal bore 12 of the anchor 10. In addition, the inner cavity 27 of the plug 20 and the shaft 31 of the locking member 30 may include surface features other than threads 28,33 for engagement of the locking member 30 with the plug 20. Also, for the purposes of this disclosure, the location of the through hole 29 may be anywhere along the length of the plug 20. The shaft 41 of the delivery device 40 is made from a biocompatible material, such as stainless steel, and is coupled to the handle 42 by having the proximal portion 41b press-fit into a through hole 43 of the handle 42. However, other materials and methods of coupling may be used.

The anchoring system 50 of the present disclosure allows a surgeon to load a suture from a previously placed anchor and secure the suture in the system 50 at a preferred tension. Furthermore, the system 50 allows for one or more sutures to be secured together at one attachment point, such as described above with the second anchor 10, or independently at several attachment points. This allows for a large area of contact between the tissue and the bone and results in a better repair.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A method of tissue repair comprising:
    inserting a first anchor into bone, the first anchor having a flexible member coupled thereto;
    passing ends of the flexible member through tissue;
    inserting a second anchor into the bone, the second anchor including an internal bore;
    providing a plug, the plug including a proximal end, a closed distal end, an internal cavity, and a hole transverse to the internal cavity;
    passing at least one end of the flexible member into the hole of the plug;
    inserting the plug into the internal bore of the second anchor; and
    inserting a locking member into the internal cavity of the plug to secure the flexible member within the internal bore of the second anchor and the tissue to the bone.

2. The method of claim 1 further comprising tensioning the flexible member before placing the locking member within the internal cavity of the plug.

3. The method of claim 1 further comprising removing the locking member and tensioning the flexible member.

4. The method of claim 1 wherein the plug includes at least one tab, wherein the tab expands into a groove located on an inner wall of the second anchor upon insertion of the locking member into the internal cavity of the plug.

5. The method of claim 4 wherein the plug includes at least two tabs, wherein the tabs expand into the groove upon insertion of the locking member into the internal cavity of the plug.

6. The method of claim 1 wherein the hole comprises a through hole.

7. The method of claim 6 further comprising passing at least one end of the flexible member into the through hole of the plug.

* * * * *